(12) United States Patent
Robinson et al.

(10) Patent No.: US 10,973,962 B2
(45) Date of Patent: Apr. 13, 2021

(54) ION EXCHANGE ENHANCED ABSORBENT SYSTEMS

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 607 days.

(21) Appl. No.: 14/150,216

(22) Filed: Jan. 8, 2014

(65) Prior Publication Data

US 2014/0200532 A1 Jul. 17, 2014

Related U.S. Application Data

(60) Provisional application No. 61/753,373, filed on Jan. 16, 2013.

(51) Int. Cl.
*A61M 1/00* (2006.01)
*A61F 13/00* (2006.01)

(52) U.S. Cl.
CPC ..... *A61M 1/0023* (2013.01); *A61F 13/00068* (2013.01); *A61M 1/0052* (2014.02); *A61M 1/0088* (2013.01); *A61M 1/0094* (2014.02); *A61M 1/008* (2013.01); *A61M 1/0096* (2014.02)

(58) Field of Classification Search
CPC ...................... A61M 1/0023; A61F 13/00068
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

International Search Report and Written Opinion for PCT/US2014/010658 dated Feb. 26, 2015.

(Continued)

*Primary Examiner* — Nicholas J Weiss
*Assistant Examiner* — Alessandro R Del Priore

(57) ABSTRACT

A system, method, and apparatus for treating a tissue site with reduced pressure includes a dressing adapted to be positioned proximate the tissue site. An absorbent may be adapted to be fluidly coupled to the manifold, and an ion exchange member may be adapted to be fluidly coupled between the manifold and the absorbent. A sealing member may be adapted to cover the tissue site to form a sealed space having the manifold disposed therein. A reduced-pressure source may be adapted to be fluidly coupled to the manifold.

14 Claims, 3 Drawing Sheets

(56) References Cited

U.S. PATENT DOCUMENTS

| | | |
|---|---|---|
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0009781 A1* | 1/2005 | Engstad .............. A61K 8/73 514/54 |
| 2006/0079852 A1 | 4/2006 | Bubb et al. |
| 2006/0107642 A1* | 5/2006 | Smith .............. A61L 9/014 55/524 |
| 2007/0066946 A1 | 3/2007 | Haggstrom et al. |
| 2007/0129707 A1* | 6/2007 | Blott .............. A61M 1/0058 604/543 |
| 2007/0148117 A1* | 6/2007 | Davis .............. A61L 15/38 424/70.13 |
| 2007/0225663 A1* | 9/2007 | Watt .............. A61M 1/0088 604/313 |
| 2008/0017578 A1* | 1/2008 | Childs .............. B01D 63/06 210/650 |
| 2009/0234307 A1 | 9/2009 | Vitaris |
| 2010/0069863 A1 | 3/2010 | Olson |
| 2010/0179493 A1 | 7/2010 | Heagle et al. |
| 2010/0286638 A1 | 11/2010 | Malhi |
| 2011/0054421 A1 | 3/2011 | Hartwell |
| 2011/0282309 A1 | 11/2011 | Adie et al. |
| 2012/0046624 A1 | 2/2012 | Locke et al. |
| 2013/0315650 A1* | 11/2013 | Cassin .............. A61K 8/06 401/196 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2466931 A | 7/2010 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 2005123170 A1 | 12/2005 |
| WO | 2008/100438 A1 | 8/2008 |
| WO | 2010/126444 A1 | 11/2010 |
| WO | PCT/EP/2011070394 | * 11/2011 .......... A61K 8/0245 |

(56) References Cited

FOREIGN PATENT DOCUMENTS

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
Partial International Search Report for corresponding PCT/US2014/010658 dated May 23, 2014.
Extended European Search Report for Corresponding Application No. 192012672, dated Jan. 7, 2020.

\* cited by examiner

ION EXCHANGE ENHANCED ABSORBENT SYSTEMS

Under 35 U.S.C. § 119(e), this application claims priority to and the benefit of U.S. Provisional Patent Application No. 61/753,373 filed Jan. 16, 2013, entitled "Ion Exchange Enhanced Absorbent Systems," the disclosure of which is hereby incorporated by reference in its entirety.

TECHNICAL FIELD

The present disclosure relates generally to medical treatment systems for treating tissue sites and processing fluids. More particularly, but not by way of limitation, the present disclosure relates to absorbent dressings having ion exchange media disposed therein.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," "negative pressure wound therapy," and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients. In particular, reduced-pressure therapy systems incorporating absorbents formed of superabsorbent polymers often experience a real world absorption capacity that is less than the rated absorption capacity. This may necessitate the use of additional absorbent or increase the number of dressing changes necessary to treat a tissue site. Increasing the amount of absorbent used and the number of dressing changes can negatively impact the ability to provide reduced-pressure therapy.

SUMMARY

According to an exemplary embodiment, a system for treating a tissue site with reduced pressure is described. The system may include a manifold adapted to be positioned adjacent the tissue site. The system may also include an absorbent adapted to be fluidly coupled to the manifold. The system may further include an ion exchange member adapted to be fluidly coupled between the manifold and the absorbent. The system may have a sealing member adapted to cover the tissue site to form a sealed space having the manifold disposed therein and a reduced-pressure source adapted to be fluidly coupled to the manifold.

According to another exemplary embodiment, a method for treating a tissue site may be described. The method may dispose a manifold proximate the tissue site and seal the manifold to the tissue site with a sealing member. The method may fluidly couple a reduced pressure source to the manifold. The method may further fluidly couple an ion exchange member having ion exchange media between the manifold and the reduced pressure source. The method may fluidly couple an absorbent between the ion exchange member and the reduced pressure source and supply reduced pressure to the tissue site to draw fluid from the tissue site to the absorbent through the ion exchange member. The method may reduce an ionic concentration of the fluid with the ion exchange member.

According to another exemplary embodiment, a dressing for treating a tissue site may be described. The dressing may include an absorbent adapted to be positioned adjacent the tissue site and an ion exchange layer adapted to be positioned between the absorbent and the tissue site. The dressing may include a sealing member adapted to be positioned over the ion exchange layer and the absorbent and further adapted to be fluidly sealed to an area adjacent the tissue site.

According to another exemplary embodiment, a container for storing fluids from a tissue site is described. The container may include a body having an interior portion, a fluid inlet, and a fluid outlet. The container may also include an absorbent positioned in the interior and adapted to absorb fluid from the tissue site. The container may further include an ion exchange member fluidly coupled to the fluid inlet.

According to another exemplary embodiment, a tube for transmitting fluid from a tissue site to a container is described. The tube may include a cylindrical body having at least one lumen; and an ion exchange insert disposed within the lumen so that fluid transmitted through the lumen passes through the ion exchange member.

Other aspects, features, and advantages of the exemplary embodiments will become apparent with reference to the drawings and detailed description that follow.

DETAILED DESCRIPTION OF ILLUSTRATIVE EMBODIMENTS

New and useful systems, methods, and apparatuses for fluid storage in a reduced-pressure therapy environment are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative exemplary embodiments, variations, and equivalents not specifically described in detail. The following detailed description should therefore be taken as illustrative and not limiting.

The exemplary embodiments may be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
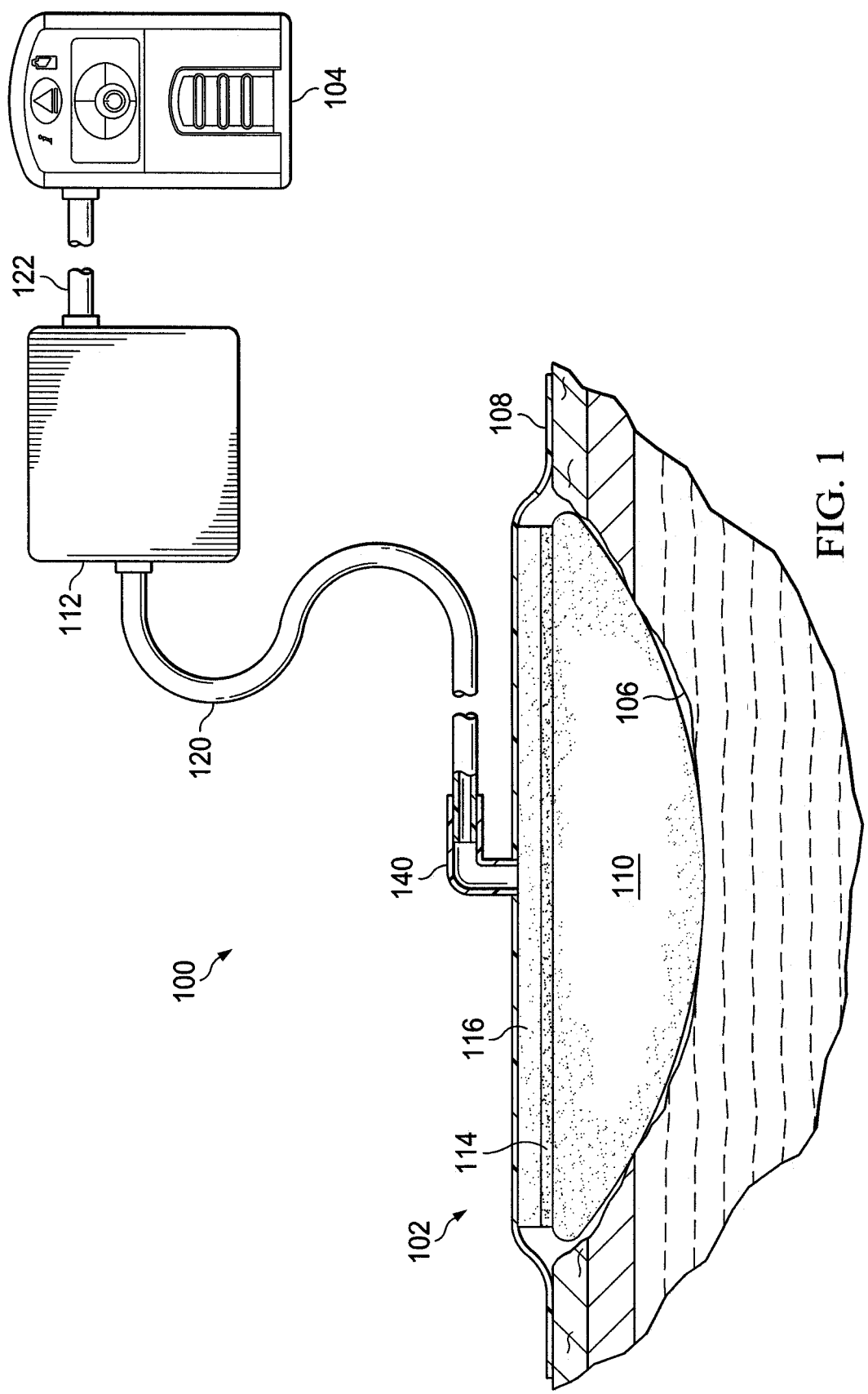
FIG. 1 is sectional view illustrating a therapy system in accordance with an exemplary embodiment.

FIG. 1 is a sectional view of one exemplary embodiment illustrating a therapy system 100 for supplying reduced pressure to a tissue site 106 that can reduce the ionic content of fluid before the fluid contacts an absorbent in accordance with this specification. In some embodiments, the therapy system 100 may include a dressing 102 fluidly coupled to a reduced-pressure source 104. A regulator or controller may also be fluidly coupled to the dressing 102 and the reduced-pressure source 104. The dressing 102 generally may include a drape, such as a drape 108, and a pressure distribution manifold, such as a manifold 110. In an exemplary embodiment, the dressing 102 may further include a reduced-pressure interface, such as a connector 140. The connector 140 is fluidly coupled to the manifold 110 for distributing reduced pressure at the tissue site 106. In some embodiments, the dressing 102 may also include an ion exchange member, such as an ion exchange layer 114, and an absorbent 116. The absorbent 116 may be disposed between the manifold 110 and the drape 108. In some exemplary embodiments, the therapy system 100 may also include a fluid container, such as a container 112, fluidly coupled to the dressing 102 by a conduit, such as a tube 120. The container 112 may be further fluidly coupled to the reduced-pressure source 104 by another conduit, such as a tube 122.

In general, components of the therapy system 100 may be coupled directly or indirectly. For example, reduced-pressure source 104 may be directly coupled to the container 112 and indirectly coupled to the dressing 102 through the container 112. Components may be fluidly coupled to each other to provide a path for transferring fluids (i.e., liquid and/or gas) between the components. In some exemplary embodiments, components may be fluidly coupled with the tube 120 and the tube 122, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some exemplary embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the manifold 110 may be placed within, over, on, or otherwise proximate a tissue site, for example the tissue site 106. The drape 108 may be placed over the manifold 110 and sealed to tissue proximate the tissue site 106. The tissue proximate the tissue site 106 is often undamaged epidermis peripheral to the tissue site 106. Thus, the dressing 102 can provide a sealed therapeutic environment proximate the tissue site 106 that may be substantially isolated from the external environment. The reduced-pressure source 104 can reduce the pressure in the sealed therapeutic environment. Reduced pressure applied uniformly through the manifold 110 in the sealed therapeutic environment can induce macrostrain and microstrain in the tissue site 106, as well as remove exudates and other fluids from the tissue site 106, which can be collected in the absorbent 116 or the container 112 and disposed of properly.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, the fluid path may also be reversed in some applications (such as by substituting a positive-pressure source for a reduced-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by the dressing 102. In many cases, the local ambient pressure may also be the atmospheric pressure at which the tissue site 106 is located. Alternatively, the pressure may be less than a hydrostatic pressure associated with tissue at the tissue site 106. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 104, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

The manifold 110 can be generally adapted to contact the tissue site 106. The manifold 110 may be partially or fully in contact with the tissue site 106. If the tissue site 106 extends into the tissue from a tissue surface, for example, the manifold 110 may partially or completely fill the tissue site 106, or may be placed over the tissue site 106. The manifold 110 may take many forms, and may have many sizes, shapes, or thicknesses depending on a variety of factors, such as the type of treatment being implemented or the nature and size of the tissue site 106. For example, the size and shape of the manifold 110 may be adapted to the contours of deep and irregular shaped tissue sites.

More generally, a manifold is a substance or structure adapted to distribute reduced pressure to a tissue site, remove fluids from a tissue site, or distribute reduced pressure to and remove fluids from a tissue site. In some exemplary embodiments, a manifold may also facilitate delivering fluids to a tissue site, for example, if the fluid path is reversed or a secondary fluid path is provided. A manifold may include flow channels or pathways that distribute fluids provided to and removed from a tissue site around the manifold. In some embodiments, the flow channels or pathways may be interconnected to improve distribution of fluids provided to or removed from a tissue site. For example, cellular foam, open-cell foam, porous tissue collections, and other porous material, such as gauze or felted mat, generally include structural elements arranged to form flow channels. Liquids, gels, and other foams may also include or be cured to include flow channels.

In some embodiments, the manifold 110 may be a porous foam material having interconnected cells or pores adapted to uniformly (or quasi-uniformly) distribute reduced pressure to the tissue site 106. The foam material may be either hydrophobic or hydrophilic. In one non-limiting example, the manifold 110 can be an open-cell, reticulated polyurethane foam such as GranuFoam® dressing available from Kinetic Concepts, Inc. of San Antonio, Tex.

In an example in which the manifold 110 may be made from a hydrophilic material, the manifold 110 may also wick fluid away from the tissue site 106, while continuing to distribute reduced pressure to the tissue site 106. The wicking properties of the manifold 110 may draw fluid away from the tissue site 106 by capillary flow or other wicking mechanisms. An example of a hydrophilic foam is a polyvinyl alcohol, open-cell foam such as V.A.C. WhiteFoam® dressing available from Kinetic Concepts, Inc. (KCI) of San Antonio, Tex. Other hydrophilic foams may include those made from polyether. Other foams that may exhibit hydrophilic characteristics include hydrophobic foams that have been treated or coated to provide hydrophilicity.

The manifold 110 may further promote granulation at the tissue site 106 when pressure within the sealed therapeutic environment is reduced. For example, any or all of the surfaces of the manifold 110 may have an uneven, coarse, or jagged profile that can induce microstrains and stresses at the tissue site 106 when reduced pressure is applied through the manifold 110 to the tissue site 106.

In some embodiments, the manifold may be constructed from bioresorable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 110 may further serve as a scaffold for new cell-growth, or a scaffold material may be used in conjunction with the manifold 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. The sealing member may be constructed from a material that can provide a fluid seal between two components or two environments, such as between a therapeutic environment and a local external environment. The sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically acceptable, pressure-sensitive adhesive that extends about a periphery, a portion of, or an entirety of the sealing member. Other exemplary embodiments of an attachment device may include a double-sided tape, paste, hydrocolloid, hydrogel, silicone gel, organogel, or an acrylic adhesive.

The reduced pressure developed by the reduced-pressure source 104 may be delivered through the tube 120 to the connector 140. The connector 140 may be a device configured to fluidly couple the reduced-pressure source 104 to the sealed therapeutic environment formed by the drape 108. In some exemplary embodiments, the connector 140 may include a flange portion that couples to the drape 108 and a port portion that fluidly couples to the tube 120. The port portion is fluidly sealed to the flange portion and provides fluid communication through the flange portion so that connector 140 may cover an aperture in the drape 108 to prevent fluid communication between the sealed therapeutic environment and the ambient environment while allowing fluid communication through the drape 108 between the sealed therapeutic environment and the tube 120. In some embodiments, the connector 140 may be a T.R.A.C.® Pad or Sensa T.R.A.C.® Pad available from KCI of San Antonio, Tex. In other exemplary embodiments, the connector 140 may also be a conduit inserted through the drape 108.

The container 112 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy. Some exemplary embodiments of the therapy system 100 may not include the container 112;

instead, these exemplary embodiments of the therapy system 100 handle fluid storage with the dressing 102 and the absorbent 116 as described in more detail below.

The ion exchange layer 114 may be formed of an ion exchange media (IEM). IEM may be adapted to provide an exchange of ions between two electrolytes, or between an electrolyte solution and a complex. An electrolyte may be a compound that ionizes when dissolved in a suitable ionizing solvent, such as water. An electrolyte solution may contain a dissolved salt, such as NaCl. A complex may be an atom or ion having a surrounding array of bound molecules or anions known as ligands or complexing agents. IEM works by replacing cations and anions in an electrolyte or an electrolyte solution as the electrolyte or electrolyte solution interacts with the IEM. Cations are ions having a net positive charge, for example, $Na^+$. Cations may be replaced in the electrolyte or electrolyte solution with hydrogen (H+) ions of the IEM. Anions are ions having a net negative charge, for example, Cl−. Anions may be replaced in the electrolyte or electrolyte solution with hydroxyl (OH−) ions of the IEM. The H+ and OH− ions may combine in the electrolyte or electrolyte solution to form water. The IEM is typically in the form of porous beads that are formed from crosslinked polymers, such as polystyrene, that are doped or grafted with acidic polymers. An example of an acidic polymer may include poly(2-acrylamido-2-methyl-1-propanesulfonic acid) or polyAMPS. The polyAMPS exchange positively charged salt ions for H+. Another example of an acidic polymer may include poly(acrylamido-N-propyltrimethylammonium chloride) or polyAPTAC. The polyAPTAC exchange negatively charged salt ions for OH−.

The IEM may include a mixture of cation absorbing media and anion absorbing media to form a mixed bed media that simultaneously absorbs both anions and cations. Non-limiting examples of the mixed bed media include Amberlite IRN150 and TMD-8. The IEM may be formed of ion exchange resins, zeolites, montmorillonite, bentonites, clay, or soil humus, for example. Ion exchange resins, also known as ion exchange polymers, are insoluble matrices normally in the form of small beads fabricated from an organic polymer substrate. Ion exchange resins may have pores on the surface that trap and release ions. Ion exchange resins can include crosslinked polystyrene, for example. Zeolites are microporous, aluminosilicate minerals. Zeolites have a porous structure that allow cations, such as $Na^+$, $K^+$, $Ca^{2+}$, and $Mg^{2+}$, for example, to be accommodated by the zeolite. Common zeolites include analcime, chabazite, clinoptilolite, heulandite, natrolite, phillipsite, and stilbite, for example. In addition to the above materials, other ion exchange media include activated charcoal, both particulate and in the form of fabrics or non-wovens, for example, and Zorflex, also known as Chemviron Carbon. Chemviron Carbon may also be known as 100% activated carbon.

The absorbent 116 is an example of a material used to hold, stabilize and/or solidify fluids that may be collected from the tissue site 106. The absorbent 116 may be positioned in the dressing 102, in the container 112, and in other places of the therapy system 100 where fluid absorption may be desired. In some exemplary embodiments, the absorbent 116 may be formed of a superabsorbent polymer (SAP). Generally, relative to their mass, SAPs can absorb and retain large quantities of liquid, and in particular water. Many medical disposables, such as canisters and dressings, use SAPs to hold and stabilize or solidify wound fluids. The SAPs used to form the absorbent 116 may be of the type often referred to as "hydrogels," "super-absorbents," or "hydrocolloids." When disposed within the dressing, such as the dressing 102, the SAPs may be formed into fibers or spheres to manifold reduced pressure until the SAPs become saturated. Spaces or voids between the fibers or spheres may allow a reduced pressure that is applied to the dressing 102 to be transferred within and through the absorbent 116. In some embodiments, fibers of the absorbent 116 may be either woven or non-woven.

The SAPs may be formed in several ways, for example, by gel polymerization, solution polymerization, or suspension polymerization. Gel polymerization may involve blending of acrylic acid, water, cross-linking agents, and ultraviolet (UV) initiator chemicals. The blended mixture may be placed into a reactor where the mixture is exposed to UV light to cause crosslinking reactions that form the SAP. The mixture may be dried and shredded before subsequent packaging and/or distribution. Solution polymerization may involve a water based monomer solution that produces a mass of reactant polymerized gel. The monomer solution may undergo an exothermic reaction that drives the cross-linking of the monomers. Following the crosslinking process, the reactant polymer gel may be chopped, dried, and ground to its final granule size. Suspension polymerization may involve a water-based reactant suspended in a hydrocarbon-based solvent. However, the suspension polymerization process must be tightly controlled and is not often used.

SAPs absorb liquids by bonding with water molecules through hydrogen bonding. Hydrogen bonding involves the interaction of a polar hydrogen atom with an electronegative atom. As a result, SAPs absorb water based on the ability of the hydrogen atoms in each water molecule to bond with the hydrophilic polymers of the SAP having electronegative ionic components. High absorbing SAPs are formed from ionic crosslinked hydrophilic polymers such as acrylics and acrylamides in the form of salts or free acids. Because the SAPs are ionic, they are affected by the soluble ionic components within the solution being absorbed and will, for example, absorb less saline than pure water. The lower absorption rate of saline is caused by the sodium and chloride ions blocking some of the water absorbing sites on the SAPs. If the fluid being absorbed by the SAP is a solution containing dissolved mineral ions, fewer hydrogen atoms of the water molecules in the solution may be free to bond with the SAP. Thus, the ability of an SAP to absorb and retain a fluid may be dependent upon the ionic concentration of the fluid being absorbed. For example, an SAP may absorb and retain de-ionized water up to 500 times the weight of the dry SAP. In volumetric terms, an SAP may absorb fluid volumes as high as 30 to 60 times the dry volume of the SAP. Other fluids having a higher ionic concentration may be absorbed at lower quantities. For example, an SAP may only absorb and retain a solution that is 0.9% salt (NaCl) up to 50 times the weight of the dry SAP. Since wound fluids contain salts, such as sodium, potassium, and calcium, the absorption capacity of the SAP may be significantly reduced. The reduction in absorption capacity may necessitate using additional SAP that can significantly add to the overall bulkiness of the dressing or fluid storage device. In addition, in many therapy systems, using additional SAP may not be possible due to size limitations of the dressing or container. In other therapy systems, using additional SAP may not be possible because the increase SAP may decrease the ability of the system to distribute the reduced pressure through the saturated SAP.

As disclosed herein, the therapy system 100 can overcome these shortcomings and others by providing a system that may include an IEM positioned between the tissue site and an absorbent. The IEM may reduce the number of ionized particles within the wound fluid, allowing for greater absorption of the wound fluid by the SAPs forming the absorbent. For example, in some exemplary embodiments of the therapy system 100, the IEM may be placed between the manifold and the absorbent in the dressing so that wound fluid drawn out of the tissue site passes through an ion exchange layer before reaching the absorbent. In other exemplary embodiments, the IEM may be positioned within the tube fluidly coupling the tissue site and the container that may be filled with an absorbent formed from SAPs. In another exemplary embodiment, the IEM may be positioned proximate the fluid inlet of the container. In general, the IEM may be positioned between the tissue site and the fluid storage device so that the fluid from the tissue site passes through the IEM before reaching the absorbent of the fluid storage device.

Figure 2:
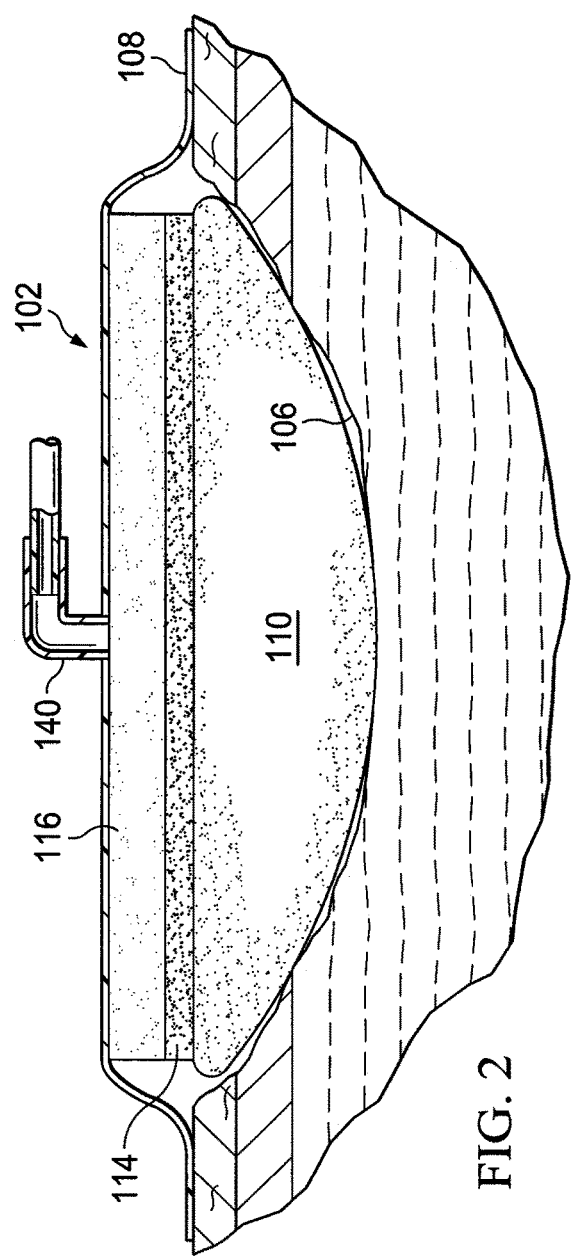
FIG. 2 is a sectional view illustrating an exemplary embodiment of a dressing of the therapy system of FIG. 1.

FIG. 2 is a sectional view illustrating additional details of the dressing 102. The ion exchange layer 114 having IEM may be positioned between the manifold 110 and the absorbent 116. The ion exchange layer 114 may be a layer having a first side, a second side, and a thickness between the first side and the second side. In some exemplary embodiments, the IEM forming the ion exchange layer 114, such as, ion exchange resins, may be coated onto a wicking substrate layer and crosslinked to form the ion exchange layer 114. Before crosslinking, the ion exchange resins may be coated onto a fabric or non-woven material. If the ion exchange resins are coated onto a non-woven material, the resulting ion exchange layer 114 may be an integral component of the dressing 102. In some embodiments, the ion exchange layer 114 may be formed around the absorbent 116, enabling ionic components to be removed before the wound fluid is exposed to the SAP. If the ion exchange resins are coated onto a fabric, the ion exchange layer 114 may a non-integral component of the dressing 102. In some embodiments, the first side of the ion exchange layer 114 may be disposed adjacent the manifold 110, and the absorbent 116 may be disposed adjacent the second side of the ion exchange layer 114. The first side of the ion exchange layer 114 may have a surface area that is less than the surface area of a side of the manifold 110 that is adjacent the ion exchange layer 114. In other exemplary embodiments, the first side of the ion exchange layer 114 may have a surface area that is equal to or greater than the surface area of a side of the manifold 110 that is adjacent the ion exchange layer 114. The thickness of the ion exchange layer 114 may depend, in part, on the expected ionic concentration of the fluids received from the tissue site 106.

The absorbent 116 may include a first side, a second side, and a thickness between the first side and the second side. The first side of the absorbent 116 may be disposed adjacent the second side of the ion exchange layer 114. As shown, the first side of the absorbent 116 may have a surface area that may be substantially equivalent to the surface area of the second side of the ion exchange layer 114. In other exemplary embodiments, the surface area of the first side of the absorbent 116 may be greater than or less than the surface area of the second side of the ion exchange layer 114. In some embodiments, the thickness of the absorbent 116 may be greater than the thickness of the ion exchange layer 114. In other exemplary embodiments, the thickness of the absorbent 116 may be less than or equal to the thickness of the ion exchange layer 114.

The drape 108 may be positioned over the absorbent 116 adjacent the second side of the absorbent 116. In some embodiments, the drape 108 may cover the entirety of the absorbent 116 and the ion exchange layer 114 and couple to the tissue proximate the tissue site 106. The connector 140 may be coupled to the drape 108 and fluidly coupled to the absorbent 116 and the manifold 110 through an aperture in the drape 108.

In operation, reduced pressure may be supplied to the absorbent 116 and the manifold 110 through the connector 140. The reduced pressure draws fluids out of the tissue site 106, and the manifold 110 distributes the fluids from the tissue site 106 to the ion exchange layer 114. The fluids drawn from the tissue site 106 may have a high ionic concentration. The fluids may pass through the ion exchange layer 114 where the IEM may reduce the ionic concentration of the fluid by exchanging cations and anions in the fluid for $H+$ and $OH-$ ions in the ion exchange layer 114 before the fluid moves into the absorbent 116. The fluid passing from the ion exchange layer 114 into the absorbent 116 may have a reduced ionic concentration, allowing for increased absorption efficiency by the absorbent 116. In some exemplary embodiments, the surface area of the manifold 110 that is adjacent the first side of the ion exchange layer 114 and the surface area of the absorbent 116 that is adjacent the second side of the ion exchange layer 114 may be substantially the same. The equivalent surface areas may increase the amount of fluid that passes through the ion exchange layer 114 before entering the absorbent 116, which may further increase the absorption efficiency of the absorbent 116.

Figure 3:
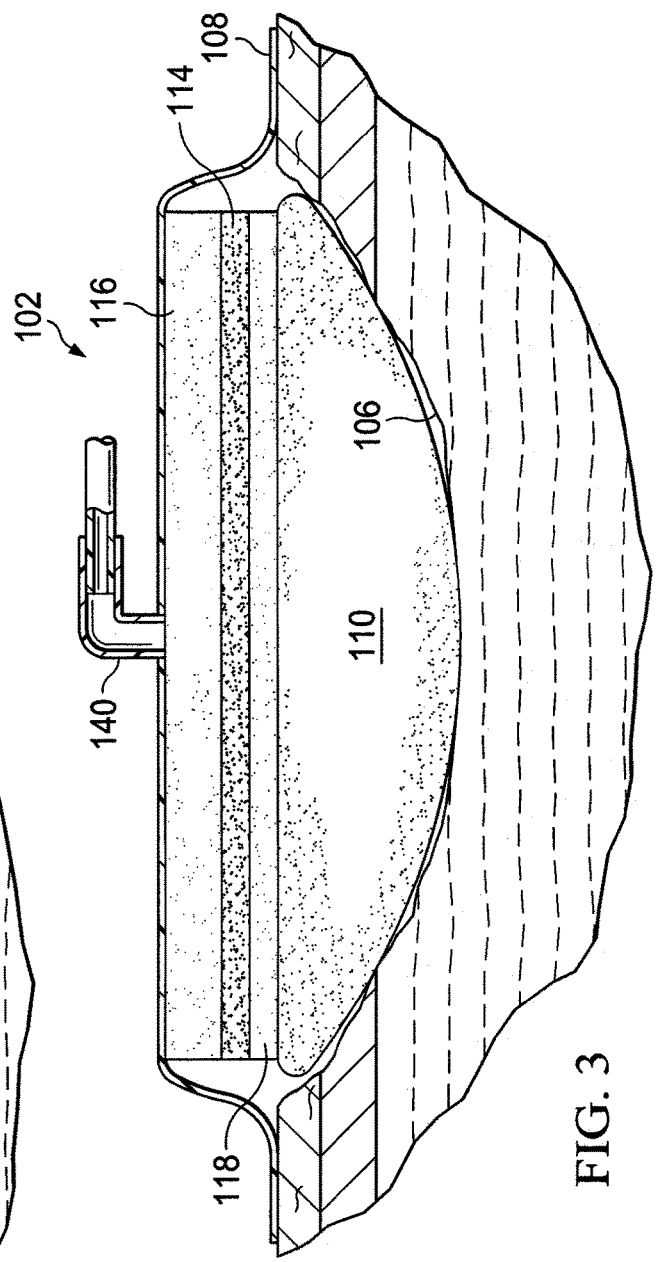
FIG. 3 is a sectional view illustrating another exemplary embodiment of the dressing of the therapy system of FIG. 1.

FIG. 3 is a sectional view illustrating additional details of another exemplary embodiment of the dressing 102. The dressing 102 may include the ion exchange layer 114, the absorbent 116 and a separate wicking layer 118. The ion exchange layer 114 of FIG. 3 may be formed of beads bound together, for example, by being sandwiched between two fluid permeable layers, to form a layer having a first side, a second side, and a thickness between the first side and the second side. The wicking layer 118 may be a layer of wicking material configured to draw fluid toward the ion exchange layer 114. The wicking material may be a material suitable for disposition adjacent the manifold 110 or the tissue site 106 and configured to draw fluid into and through the material based on capillary action. In some exemplary embodiments, the wicking material may be a porous material. In other exemplary embodiments, the wicking material may be a non-porous material. The exemplary embodiment of FIG. 3 may operate in a manner similar to the exemplary embodiment of FIG. 2.

Figure 4:
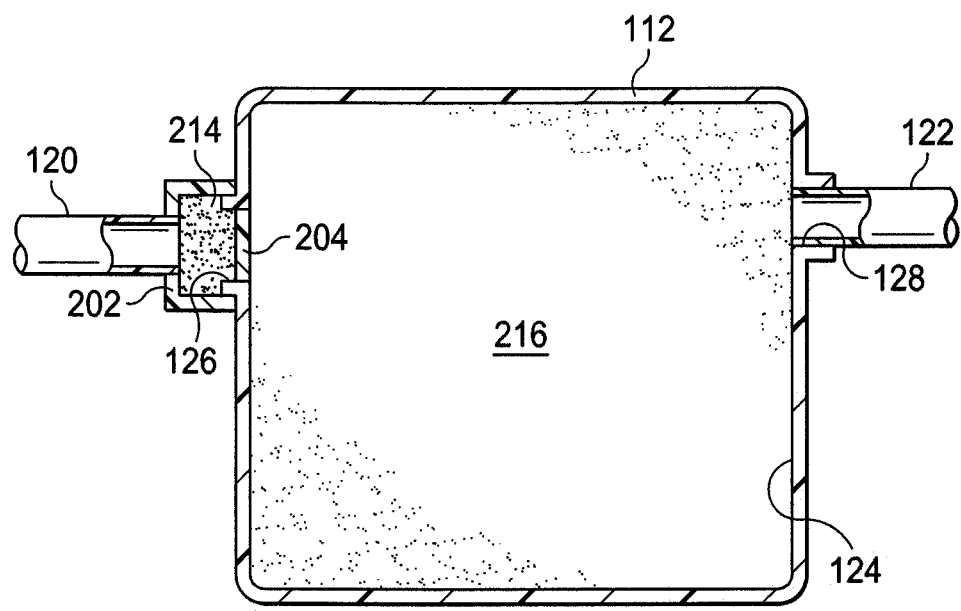
FIG. 4 is a sectional view illustrating a container of another exemplary embodiment of the therapy system of FIG. 1.

FIG. 4 is a sectional view illustrating additional details of the container 112. In some embodiments, the container 112 comprises a body having an interior 124. In some embodiments, an absorbent 216 may be disposed within the interior 124 of the container 112. The absorbent 216 may be similar to the absorbent 116 described above with respect to FIGS. 1-3. In some exemplary embodiments, the absorbent 216 may substantially fill the interior 124. In other exemplary embodiments, the absorbent 216 may fill only a portion of the interior 124. The interior 124 of the container 112 may be adapted to allow for the absorbent 216 to expand if the absorbent 216 absorbs fluid from the tissue site 106. In some embodiments, the container 112 may be rigid, and the absorbent 216 may not substantially fill the interior 124, leaving sufficient space to allow for expansion of the absorbent 216. In some embodiments, the container 112 may be flexible, and the interior 124 may be configured to expand to accommodate expansion of the absorbent 216. In addition, the amount and disposition of the absorbent 216 within the interior 124 may vary as needed to allow fluid communication of reduced pressure through the container 112 to the dressing 102.

The container 112 may further include a fluid inlet 126 and a fluid outlet 128. In some embodiments, the fluid inlet 126 passes through a wall of the container 112 to provide fluid communication between the interior 124 and an area outside of the container 112. In some embodiments, the tube 120 may fluidly couple to the fluid inlet 126 so that the fluid inlet 126 may provide fluid communication between the dressing 102 and the interior 124. The fluid outlet 128 may extend through a wall of the container 112 to provide fluid communication between the interior 124 and an area outside of the container 112. In some embodiments, the tube 122 may be fluidly coupled to the fluid outlet 128 and may be further fluidly coupled to the reduced-pressure source 104, allowing for fluid communication between the reduced-pressure source 104 and the interior 124. The fluid inlet 126 and the fluid outlet 128 may be positioned on the container 112 as shown in FIG. 4. In other embodiments, the fluid inlet 126 and the fluid outlet 128 may be positioned in other locations to accommodate additional components of the therapy system 100. For example, the container 112 may be combined with the reduced-pressure source 104. In this example, the fluid inlet 126 and the fluid outlet 128 may be disposed on other portions of the container 112 to accommodate the positioning of various components of the combined container 112 and reduced-pressure source 104.

In some embodiments, the container 112 may include an ion exchange housing 202. The ion exchange housing 202 may include a chamber having an inlet fluidly coupled to the tube 120 and an outlet fluidly coupled to the fluid inlet 126 of the container 112. An ion exchange member 214 having IEM may be disposed within the chamber of the ion exchange housing 202. The ion exchange member 214 may be similar to and may include the components of the ion exchange layer 114 described above with respect to FIGS. 1-3. The ion exchange member 214 may substantially fill the chamber of the ion exchange housing 202 so that fluid entering the chamber may interact with the ion exchange member 214. The ion exchange housing 202 may be coupled adjacent the fluid inlet 126 so that the chamber of the ion exchange housing 202 is in fluid communication with the fluid inlet 126. In some exemplary embodiments, a filter 204 may be positioned in the fluid inlet 126 so that the ion exchange member 214 may not migrate into the interior 124 of the container 112. In some embodiments, the filter 204 may prevent particulates from the tissue site 106 from entering the interior 124 of the container 112. The tube 120 may be fluidly coupled to the fluid inlet of the ion exchange housing 202 so that fluid in the tube 120 may be in fluid communication with the chamber of the ion exchange housing 202. In other embodiments, the ion exchange housing 202 may be a separate component or positioned on other portions of the container 112, provided that the fluid communication path between the dressing 102 and the absorbent 216 passes through the ion exchange housing 202 and the ion exchange member 214.

In operation, the reduced-pressure source 104 may supply reduced pressure to the interior 124 of the container 112 through the fluid outlet 128 and the tube 122. The reduced pressure may be communicated through the interior 124 to the fluid inlet 126 and the tube 120, where the reduced pressure may be further communicated to the dressing 102 and the tissue site 106. Fluid passing from the tube 120 into the interior 124 may pass through the ion exchange member 214. The reduced pressure may draw fluids out of the tissue site 106 and the manifold 110 may distribute the fluids from the tissue site 106 to the connector 140 and the tube 120. The fluids drawn from the tissue site 106 may have a high ionic concentration. The fluids may communicate through the tube 120 into the interior of the ion exchange housing 202, where the fluids pass through the ion exchange member 214. The ion exchange member 214 reduces the ionic concentration of the fluid, as described above, before the fluid passes into the interior 124 of the container 112. The fluid passing through the ion exchange member 214 into the interior 124 may have a reduced ionic concentration, allowing for increased absorption efficiency by the absorbent 216 disposed within the interior 124.

Figure 5:
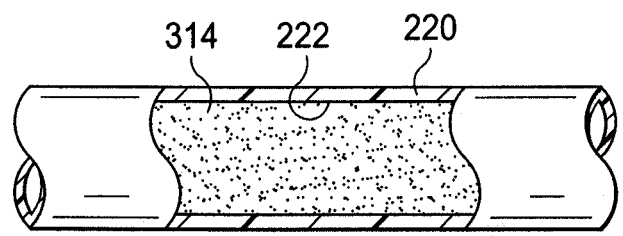
FIG. 5 is a sectional view illustrating a tube of another exemplary embodiment of the therapy system of FIG. 1.

FIG. 5 is a sectional view of a tube 220 illustrating additional details that may be associated with some embodiments. The tube 220 may be similar to the tube 120 described above. The tube 220 of FIG. 5 may fluidly couple the dressing 102 to the container 112 in a manner similar to that of the tube 120 of FIG. 1. The tube 220 may include at least one lumen 222 that may contain an ion exchange insert 314 having IEM. The ion exchange insert 314 may be similar to the ion exchange layer 114 and the ion exchange member 214 described above with respect to FIGS. 1-4. The ion exchange insert 314 may substantially fill the lumen 222. In some embodiments, the ion exchange insert 314 may permit fluid communication through the lumen 222 of the tube 220 so that fluid drawn from the tissue site 106 may be fluidly communicated from the dressing 102 to the container 112 through the lumen 222 of the tube 220. In some exemplary embodiments, the tube 220 may have multiple lumens. For example, the tube 220 may have a first lumen substantially filled with the ion exchange insert 314 and a second lumen substantially filled with an absorbent. In other exemplary embodiments, the lumen 222 of the tube 220 may only be partially filled with the ion exchange insert 314. For example, a portion of the lumen 222 proximate the manifold 110 may be substantially filled with the ion exchange insert 314, and another portion of the lumen 222 proximate the reduced-pressure source 104 may be filled with an absorbent.

In operation, the reduced-pressure source 104 may supply reduced pressure to the container 112 and the tube 220, where the reduced pressure may be further communicated to the dressing 102 and the tissue site 106. The reduced pressure may draw fluids out of the tissue site 106 and the manifold 110 may distribute the fluids from the tissue site 106 to the connector 140 and the tube 220. The fluids drawn from the tissue site 106 may have a high ionic concentration. As the fluids are communicated through the tube 220 into the container 112, the fluids may pass through the ion exchange insert 314. The ion exchange insert 314 may reduce the ionic concentration of the fluid, as described above, before the fluid passes into the container 112. The fluid passing across the ion exchange insert 314 in the lumen 222 of the tube 220 may have a reduced ionic concentration, allowing for increased absorption efficiency by an absorbent disposed within the container 112.

Some exemplary embodiments may include a combination of the components of FIGS. 2-5. For example, the ion exchange layer 114 may be used with the container 112. In these exemplary embodiments, the container 112 may include the ion exchange housing 202 or may not include the ion exchange housing 202. In other embodiments, the ion exchange layer 114 may be used with the tube 220 and the ion exchange insert 314. In these exemplary embodiments, the tube 220 may also include an absorbent, or the container 112 may be fluidly coupled to the tube 220 opposite the manifold 110. In still other embodiments, the tube 220 having the ion exchange insert 314 may be used with the container 112 having the ion exchange housing 202 and the ion exchange member 214. Each exemplary embodiment may be used with the other disclosed exemplary embodiments provided that the IEM may be positioned between the manifold 110 and the absorbent 116 or the absorbent 216, for example.

The systems and methods described herein may provide significant advantages, some of which have already been mentioned. For example, the therapy system may include a SAP absorbent in the dressing having an increased absorbent capacity compared to standard dressings. The increased absorbent capacity may allow the amount of SAP used in a dressing or container to be reduced, enabling a smaller dressing or container to be used. In addition, using less absorbent provides a potential cost savings over standard dressings. The systems and methods described herein also improve the efficiency of the absorbent used in dressings. Less SAP may be required to form the absorbent for fluid storage. Using less SAP may enable a low profile dressing to be formed. Using less SAP may decrease the cost to produce the absorbent and decrease the cost of other materials, such as drapes or wicking layers, for example.

It should be apparent from the foregoing that embodiments having significant advantages has been provided. While shown in only a few forms, the systems and methods illustrated are susceptible to various changes and modifications without departing from the spirit thereof.

Although certain illustrative, non-limiting, exemplary embodiments have been presented, it should be understood that various changes, substitutions, permutations, and alterations can be made without departing from the scope the appended claims. It will be appreciated that any feature that is described in connection to any one exemplary embodiment may also be applicable to any other exemplary embodiment.

It will be understood that the benefits and advantages described above may relate to one exemplary embodiment or may relate to several exemplary embodiments. It will further be understood that reference to "an" item refers to one or more of those items.

The steps of the methods described herein may be carried out in any suitable order, or simultaneously where appropriate.

Where appropriate, features of any of the exemplary embodiments described above may be combined with features of any of the other exemplary embodiments described to form further examples having comparable or different properties and addressing the same or different problems.

It will be understood that the above description of preferred exemplary embodiments is given by way of example only and that various modifications may be made by those skilled in the art. The above specification, examples and data provide a complete description of the structure and use of exemplary embodiments of the invention. Although various exemplary embodiments of the invention have been described above with a certain degree of particularity, or with reference to one or more individual exemplary embodiments, those skilled in the art could make numerous alterations to the disclosed exemplary embodiments without departing from the scope of the claims.

We claim:

1. A system for treating a tissue site with reduced pressure, the system comprising:
   a manifold adapted to be positioned adjacent the tissue site;
   an ion exchange member adapted to be fluidly coupled to the manifold and adapted to reduce an ionic concentration of fluid from the tissue site;
   an absorbent adapted to be fluidly coupled to the manifold and the ion exchange member and adapted to stabilize the fluid from the tissue site;
   a sealing member adapted to cover the tissue site to form a sealed space having the manifold disposed therein; and
   a reduced-pressure source adapted to be fluidly coupled to the manifold, the ion exchange member, and the absorbent, wherein the reduced-pressure source is adapted to draw the fluid from the tissue site, through the ion exchange member, and into the absorbent.

2. The system of claim 1, wherein the ion exchange member is positioned between the manifold and the sealing member.

3. The system of claim 1, wherein the ion exchange member is positioned between the manifold and the sealing member, and the absorbent is positioned between the ion exchange member and the sealing member.

4. The system of claim 1, wherein the ion exchange member is positioned between the manifold and the sealing member, and the system further comprises a tube fluidly coupled between the manifold and the reduced-pressure source, wherein the absorbent is disposed within the tube.

5. The system of claim 1, wherein the ion exchange member is positioned between the manifold and the sealing member and the system further comprises a container fluidly coupled between the manifold and the reduced-pressure source, wherein the absorbent is disposed within the container.

6. The system of claim 1, further comprising a tube fluidly coupled between the manifold and the reduced-pressure source, the tube having at least one lumen, and wherein the ion exchange member is disposed in the lumen of the tube.

7. The system of claim 1, further comprising:
   a tube fluidly coupled between the manifold and the reduced-pressure source, the tube having at least one lumen; and
   wherein the ion exchange member is positioned in at least a portion of the lumen of the tube and the absorbent is positioned in another portion of the lumen of the tube.

8. The system of claim 1, further comprising:
   a container fluidly coupled between the reduced-pressure source and the manifold; and
   a tube fluidly coupled between the manifold and the container, the tube having at least one lumen;
   wherein the ion exchange member is positioned in the lumen of the tube and the absorbent is disposed in the container.

9. The system of claim 1, further comprising a container having the absorbent disposed therein, the container fluidly coupled between the manifold and the reduced-pressure source, the ion exchange member fluidly coupled to a fluid inlet of the container.

10. The system of claim 1, wherein the ion exchange member comprises porous beads formed from crosslinked polymers doped or grafted with acidic polymers.

11. The system of claim 1, wherein:
    the ion exchange member comprises porous beads formed from crosslinked polymers doped or grafted with acidic polymers;
    the crosslinked polymers comprise polystyrene; and
    the acidic polymers comprise poly (2-acrylamido-2-methyl-1-propanesulfonic acid) and poly (acrylamido-N-propyltrimethylammonium chloride).

12. The system of claim 1, wherein the ion exchange member comprises a zeolite.

13. The system of claim 1, wherein the ion exchange member comprises activated charcoal.

14. The system of claim 1, wherein the ion exchange member comprises 100% activated carbon.

* * * * *